United States Patent [19]

Crawford

[11] 4,317,779

[45] Mar. 2, 1982

[54] ALPHA-SULFOXIDE AND ALPHA-SULFONE CARBOXYL COMPOUNDS

[75] Inventor: Robert J. Crawford, Wyoming, Ohio

[73] Assignee: The Procter & Gamble Company, Cincinnati, Ohio

[21] Appl. No.: 180,213

[22] Filed: Aug. 21, 1980

[51] Int. Cl.[3] ....................... C07C 143/90; C11D 1/28

[52] U.S. Cl. .................................... 260/400; 260/401; 252/121; 252/549

[58] Field of Search ................................ 260/401, 400

[56] References Cited

U.S. PATENT DOCUMENTS

| | | | |
|---|---|---|---|
| 2,159,967 | 5/1939 | Engelmann | 260/404 |
| 2,743,236 | 4/1956 | Morris et al. | 252/117 |
| 2,787,595 | 4/1957 | Webb | 252/530 |
| 3,247,258 | 4/1966 | Anderson | 568/37 |
| 3,288,859 | 11/1966 | Lyness et al. | 568/37 |
| 3,290,254 | 12/1966 | Anderson | 252/530 |
| 3,336,233 | 8/1967 | Lyness et al. | 252/549 |
| 3,929,678 | 12/1975 | Laughlin et al. | 252/526 |

FOREIGN PATENT DOCUMENTS

| | | |
|---|---|---|
| 706122 | 4/1941 | Fed. Rep. of Germany . |
| 1557063 | 2/1969 | France . |
| 54-012065 | 8/1979 | Japan . |

OTHER PUBLICATIONS

Trost et al., J. Am. Chem. Soc., 98, 4887 (1976).

*Primary Examiner*—John F. Niebling

*Attorney, Agent, or Firm*—Donald E. Hasse; Steven J. Goldstein; Richard C. Witte

[57] ABSTRACT

Alpha-sulfoxide and alpha-sulfone carboxyl compounds useful as detergent surfactants are disclosed. The compounds are particularly effective in removing greasy/oily soils under cold water laundering conditions. Detergent compositions containing the compounds also preferably contain cosurfactants and builder materials.

18 Claims, No Drawings

ALPHA-SULFOXIDE AND ALPHA-SULFONE CARBOXYL COMPOUNDS

TECHNICAL FIELD

The present invention relates to compounds containing a sulfoxide or sulfone group at the alpha-carbon atom of the parent carboxylic acid. The compounds herein are particularly useful as detergent surfactants which provide outstanding cleaning of greasy/oily type soils in cool or cold water fabric laundering operations. Excellent particulate soil removal performance can also be obtained, while maintaining the greasy/oily soil detergency, by combining the present compounds with common detergent adjunct materials, especially anionic and zwitterionic surfactants.

There has been considerable demand for detergent compositions which provide improved cleaning under cool or cold water washing conditions (5° C. to 35° C.). This is primarily due to the increasing cost of the energy required to heat water for laundering operations. However, there are many other benefits to be obtained from cold water laundering of fabrics. For example, dye transfer between fabrics is diminished, thereby making it possible to launder mixed colors without "sorting". Laundering in cold water also results in less wrinkling of fabrics, and avoids damage (shrinkage, etc.) to delicate fabrics which should not be washed in hot water.

There is also a need for new detergent surfactants to replace the increasingly expensive petroleum-based surfactants commonly used in the detergent industry. The present alpha-sulfoxide and alpha-sulfone compounds can be manufactured from renewable resources, i.e., animal and vegetable fats and oils, and thus are potentially less expensive and their supply more stable than the petroleum-based surfactants.

BACKGROUND ART

Various sulfoxide compounds are known in the art as detergent surfactants, as evidenced by the following references.

U.S. Pat. No. 2,787,595, Webb, issued Apr. 2, 1957, discloses sulfoxides of the formula $RSOR^1$, where R is methyl or ethyl and $R^1$ is a $C_9$–$C_{22}$ (preferably $C_{10}$–$C_{12}$) alkyl group, as detergent surfactants which are said to clean synergistically when combined with other surfactants.

French Pat. No. 1,557,063, Lyness, issued Feb. 14, 1969, describes alkylethoxylate sulfoxides as detergent surfactants especially effective in cold water. The $C_{10}$–$C_{14}$ alkyl methyl sulfoxides containing about 3 ethylene oxide groups are said to be the preferred cold water surfactants.

U.S. Pat. No. 3,288,859, Lyness, et al., issued Nov. 29, 1966, describes gamma-hydroxyalkyl methyl sulfoxides as excellent cool water (60°–90° F.) surfactants. Detergent compositions also containing conventional builders and other detergent adjunct materials, including anionic, nonionic, zwitterionic or cationic surfactants, are described.

U.S. Pat. No. 3,290,254, Anderson, issued Dec. 6, 1966, discloses methyl-beta-hydroxydodecyl sulfoxide as a detergent surfactant.

U.S. Pat. No. 3,929,678, Laughlin et al., issued Dec. 30, 1975, discloses ethoxylated zwitterionic compounds having improved particulate soil removal capability. The compounds are combined with organic cosurfactants, which can include various sulfoxides as a nonionic surfactant.

In addition, Trost, et al., *J. Am. Chem. Soc.*, 98, 4887 (1976), describe the preparation of ethyl alpha-methylsulfinyl decanoate for use as an intermediate in the synthesis of alpha, beta-unsaturated carbonyl compounds. The unsaturated compounds are themselves useful in the synthesis of other compounds, including pheromones of the honey bee.

The above patents and publications are incorporated herein by reference.

SUMMARY OF THE INVENTION

The present invention encompasses compounds of the formula

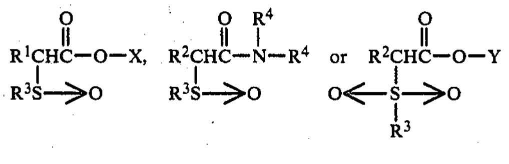

wherein $R^1$ is a $C_{10}$–$C_{18}$ hydrocarbyl group; $R^2$ is a $C_6$–$C_{18}$ hydrocarbyl group; $R^3$ is a $C_1$–$C_4$ hydrocarbyl group; each $R^4$ is hydrogen, a $C_1$–$C_4$ hydrocarbyl group, or a $C_2$–$C_3$ alkylene oxide group, or mixtures thereof, containing from about 1 to about 10 alkylene oxide units; X is an $R^4$ group or a water-soluble metal, ammonium or substituted ammonium cation; and Y is hydrogen, a water-soluble metal, ammonium or substituted ammonium cation or a $C_2$–$C_3$ alkylene oxide group, or mixtures thereof, containing from about 1 to about 10 alkylene oxide units. The present invention also encompasses detergent compositions comprising the above-described compounds.

DETAILED DESCRIPTION OF THE INVENTION

The alpha-sulfoxide and alpha-sulfone compounds of the present invention are particularly useful as detergent surfactants which provide outstanding greasy/oily soil removal performance in cool or cold water fabric laundering operations. They may, of course, also be effectively used in warm or hot water, according to the desires of the user. However, the greatest performance advantage is obtained by using the present compounds in cold water.

While not intending to be limited by theory, it is believed that the compounds herein, especially the alpha-sulfoxides, are excellent wetting agents which provide rapid penetration of the detergent solution into fabrics and soils contained therein. The increased kinetics of the detergency, even in cold water, results in superior cleaning performance.

In the general formula for the compounds herein, $R^1$ can be any $C_{10}$–$C_{18}$ hydrocarbyl group and $R^2$ can by any $C_6$–$C_{18}$ hydrocarbyl group. For example, they can be straight or branched-chain alkyl, alkenyl, alkynyl, alkaryl (e.g., alkylphenyl, alkylbenzyl), substituted hydrocarbyl (e.g., hydroxyalkyl), and the like. The nature of substituent $R^1$ and $R^2$ can be varied by the selection of the parent carboxylic acid used in the reaction scheme for making the present compounds, as disclosed hereinafter. (Although the alpha-substituted alkaryl and unsaturated carboxylic acids are not readily available via the process described in U.S. Pat. No. 4,148,811, Crawford, issued Apr. 10, 1979, they can be prepared using other, known reactions).

It is preferred that $R^1$ be a $C_{10}$–$C_{14}$ alkyl group, even more preferably a $C_{10}$–$C_{12}$ alkyl group, and that $R^2$ be a $C_8$–$C_{14}$ alkyl group, even more preferably a $C_8$–$C_{12}$ alkyl group, since these compounds have superior cold water solubility relative to their longer-chain (e.g., stearic acid) counterparts. However, it will be understood that the solubility, and hydrophilic-lipophilic balance (HLB), of any of the compounds herein can easily be adjusted to a desired range by the addition of a $C_2$–$C_3$ alkylene oxide group, or mixtures thereof, containing from about 1 to about 10 alkylene oxide units at the $R^4$, X or Y substituent of the compounds herein. Such a $C_2$–$C_3$ alkylene oxide group would commonly be terminated with a hydrogen atom, but also can be terminated with a methyl, ethyl or propyl group. The presence of the alkylene oxide group in the present compounds becomes more preferred, for solubility reasons, when $R^1$ and $R^2$ are longer-chain hydrocarbyl groups within the claimed limits. The alkylene oxide group is preferably ethylene oxide, and also preferably contains from about 1 to about 5 ethylene oxide units.

Substituent $R^3$ can be any $C_1$–$C_4$ hydrocarbyl group, such as alkyl, alkenyl or hydroxyalkyl, but preferably is a methyl or ethyl group.

Each $R^4$ can be hydrogen; a $C_1$–$C_4$ hydrocarbyl group; or a $C_2$–$C_3$ alkylene oxide group, or mixtures thereof, containing from about 1 to about 10 alkylene oxide units, but preferably from about 1 to about 5 ethylene oxide units. It is preferred that $R^4$ be hydrogen or a methyl or ethyl group, especially when $R^1$ and $R^2$ are the preferred shorter-chain hydrocarbyl groups herein.

Substituent X can be an $R^4$ group or a water-soluble metal, ammonium or substituted ammonium cation. Suitable water-soluble metal cations include any of the alkali metals and alkaline earth metals. Specific examples of substituted ammonium cations include methyl-, dimethyl-, and trimethylammonium cations and quaternary ammonium cations such as tetramethyl-ammonium and dimethyl piperidinium cations and those derived from alkylamines such as ethylamine, diethylamine, triethylamine, mixtures thereof, and the like. Preferably, X is hydrogen or a water-soluble alkali metal cation, especially sodium.

Substituent Y is hydrogen, a water-soluble metal, ammonium or substituted ammonium cation or a $C_2$–$C_3$ alkylene oxide group, or mixtures thereof, containing from about 1 to about 10 alkylene oxide units. Preferably Y is hydrogen or a water-soluble alkali metal cation, especially sodium.

The economical practice of the present invention on an industrial scale ultimately depends on a ready source of alpha-halo carboxylic acids, from which the alpha-sulfoxide and alpha-sulfone compounds herein are derived. Alpha-bromo carboxylic acids, which are available via the Hell-Volhard-Zelinsky reaction are suitable starting materials. However, H—V—Z bromo acids are quite expensive. Fortunately, high quality, low cost alpha-chloro carboxylic acids suitable for use in the synthesis scheme for preparing the compounds herein are available via the process disclosed in U.S. Pat. No. 4,148,811, Crawford, issued Apr. 10, 1979, incorporated herein by reference, using tetracyanoquinodimethane (TCNQ) as the catalyst.

A preferred overall reaction scheme for preparing the alpha-sulfoxide and alpha-sulfone compounds herein from the parent alpha-chloro carboxylic acids is as follows.

Step 1: Preparation of Alpha-Chloro Acid

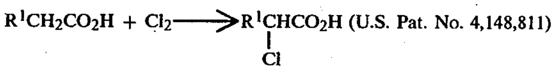

Step 2: Preparation of Alpha-Thio Acid

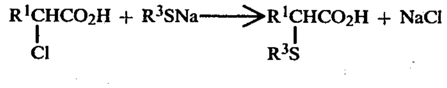

Step 3: Preparation of Alpha-Sulfinyl and Alpha-Sulfonyl Acids

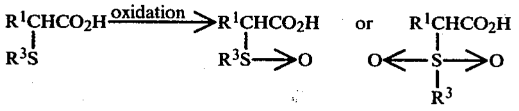

The above method of reaching the intermediate alpha-thio acids, and the derivatives thereof, is much preferred to the expensive process disclosed by Trost, et al. in *J. Am. Chem. Soc.*, 98, 4887 (1976), using lithium bases, as follows:

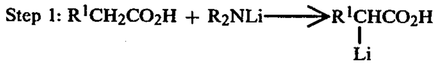

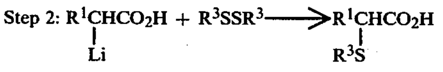

Thus, the alpha-thio and alpha-sulfoxide compounds herein also have utility as less expensive and more readily available intermediates in the preparation of the alpha, beta-unsaturated carbonyl compounds described by Trost, et al.

The preparation of alpha-sulfoxide and alpha-sulfone compounds herein is further illustrated by the following descriptions. Alpha-chlorostearic acid, obtained via the process disclosed in U.S. Pat No. 4,148,811, Crawford, cited above, is used as a representative starting material.

Preparation of Alpha-Methylthiostearic Acid: A 500 ml 3-neck round bottom flask was fitted with a mechanical stirrer, thermometer, and reflux condenser, and was charged with a solution of 19.8 g (0.30 mole) of 85% potassium hydroxide (pellets) in 100 ml of water. The solution was stirred and cooled to 0° C. in an ice bath and 11.0 ml (0.20 mole) of ice-cold methyl mercaptan was added. The resulting solution was cooled to 0° C. and 32.0 g (0.10 mole) of alpha-chlorostearic acid was added. This mixture was stirred vigorously and heated to 85° C. for 45 minutes. It was then cooled and poured into one liter of 1.5 M hydrochloric acid. The precipitated product was collected by suction filtration, washed with water, and vacuum dried to afford 32.8 g (99% yield) of alpha-methylthiostearic acid, melting point 71°–72° C.

The product was purified further by recrystallization from methanol in 89% recovery, and had a melting point of 72.5°–74° C.

Preparation of Alpha-Methylsulfinylstearic Acid: A solution of 1.27 g (0.0038 mole) of alpha-methylthiostearic acid in 15 ml of methanol was placed in a 50 ml round bottom flask equipped with a magnetic stirrer. The solution was stirred and cooled to 0° C., and 0.90 g (0.0042 mole) of solid sodium metaperiodate was added followed by 5 ml of water. The resulting mixture was allowed to stir at room temperature for 4 hours, and then was poured into 100 ml of 3 M hydrochloric acid and extracted with six 50 ml portions of chloroform. The combined chloroform solutions were washed with 100 ml of 3 M hydrochloric acid, dried with anhydrous magnesium sulfate, and evaporated to dryness. After further drying under vacuum, the product consisted of 1.20 g (90% yield) of alpha-methylsulfinylstearic acid.

This material had a melting point of 93°-97° C. after purification by recrystallization from acetonitrile (86% recovery).

Preparation of Methyl Alpha-Methylthiostearate: A 250 ml round bottom flask equipped with a magnetic stirrer and reflux condenser was charged with 50 g (0.15 mole) of alpha-methylthiostearic acid, 60 ml of 1,2-dichloroethane, and 25 ml of methanol. The resulting mixture was stirred and warmed with a heating mantle while 0.6 ml of concentrated sulfuric acid was added. It was then heated to reflux overnight. The reaction mixture was cooled, placed in a separatory funnel and washed three times with 10% aqueous sodium chloride solutions. The organic solution was dried over anhydrous magnesium sulfate and evaporated to dryness. The product was further dried under high vacuum and consisted of 50.5 g (97% yield) of methyl alpha-methylthiostearate.

The purified product was obtained in 86% recovery by recrystallization from methanol and had a melting point of 39°-40° C.

Preparation of Methyl Alpha-Methylsulfinylstearate: A one liter 3-neck round bottom flask was equipped with a magnetic stirrer, reflux condenser, and addition funnel. The flask was charged with a solution of 22.75 g (0.066 mole) of methyl alpha-methylthiostearate in 175 ml of dichloromethane. The solution was stirred at room temperature while a solution of 14.88 g (0.073 mole) of 85% meta-chloroperbenzoic acid in 175 ml of dichloromethane was added dropwise over a period of 40 minutes. The resulting mixture was then heated to reflux for 30 minutes. The solution was cooled, washed successively with 5% aqueous sodium carbonate and 10% aqueous sodium chloride solutions, dried over anhydrous magnesium sulfate and evaporated to dryness. The residue was recrystallized directly from 90 ml of acetonitrile to afford 21.8 g (92% yield) of methyl alpha-methylsulfinylstearate, melting point 56°-57° C.

Preparation of Alpha-Methylsulfinylstearamide: Alpha-methylthiostearic acid can be converted to its corresponding acid chloride by treatment with oxalyl chloride, followed by reaction of the latter with ammonia to afford alpha-methylthiostearamide. Oxidation of this intermediate with either sodium metaperiodate or meta-chloro-perbenzoic acid by the above procedures yields alpha-methylsulfinylstearamide.

Alpha-sulfonyl compounds herein are preferably derived from the corresponding alpha-thio compounds above by reaction with common oxidizing agents, such as hydrogen peroxide, peracids, organic peroxides, persulfates, hypochlorites and the like. The alpha-sulfonyl compounds can also be formed by further oxidation of the alpha-sulfinyl compounds, again using common oxidizing agents.

An alternative method of preparing the alpha-sulfoxide and alpha-sulfone compounds herein is disclosed in Japanese patent application No. 012,065, published Aug. 21, 1979, incorporated herein by reference, using alpha-bromo acids. This application describes fatty acids and their salts having an alkylsulfinyl or alkylsulfonyl substituent at the alpha-carbon position. Soaps containing these compounds, and preferably also containing anionic, nonionic or amphoteric surfactants, are said to have improved resistance against hard water and to exhibit high activity at low concentrations.

As has been described above, the alpha-sulfoxide and alpha-sulfone compounds of the present invention are particularly useful as detergent surfactants. As such, they can represent from about 0.005% to about 99%, preferably from about 3% to about 50%, more preferably from about 5% to about 25%, by weight of the detergent composition. Detergent compositions herein may be in a solid form (e.g., granules or powders), semi-solid pastes or gels, or they may be liquids.

Detergent compositions of the present invention preferably contain one or more organic cosurfactants selected from the group consisting of anionic, cationic, nonionic, ampholytic and zwitterionic surfactants, or mixtures thereof. These surfactants are described in U.S. Pat. No. 3,929,678, Laughlin et al., issued Dec. 30, 1975, incorporated herein by reference. Useful cationic surfactants also include those described in the pending U.S. patent applications Ser. No. 919,181, Murphy, and Ser. No. 919,341, Cockrell, both filed June 26, 1978, incorporated herein by reference. The cosurfactant represents from about 1% to about 50%, preferably from about 2% to about 40%, more preferably from about 3% to about 20%, by weight of the detergent composition.

The anionic and zwitterionic surfactants described above are preferred cosurfactants herein because of their ability to boost the particulate soil removal performance of detergent compositions containing the present alpha-sulfoxide or alpha-sulfone compounds, while maintaining the excellent greasy/oily soil cleaning previously described.

Useful anionic surfactants specifically include those described in U.S. Pat. No. 3,929,678, cited above, from column 23, line 57 to column 35, line 20, and those described in U.S. Pat. No. 4,199,483, Jones, issued Apr. 22, 1980, from column 5, line 3 to column 6, line 26, incorporated herein by reference.

Specific preferred anionics for use herein include: the linear $C_9$–$C_{15}$ alkylbenzene sulfonates (LAS); the branched $C_9$–$C_{15}$ alkylbenzene sulfonates (ABS); the tallow alkyl sulfates, the coconut alkyl glyceryl ether sulfonates; the sulfated condensation products of mixed $C_{10}$–$C_{18}$ fatty alcohols with from about 1 to about 14 moles of ethylene oxide; and the mixtures of higher fatty acid soaps containing from 10 to 18 carbon atoms.

A preferred weight ratio of the compounds herein to anionic surfactant is from about 1:3 to about 3:1, more preferably from about 1:1 to about 2:1.

Useful zwitterionic surfactants herein specifically include those described in the above U.S. Pat. No. 3,929,678 from column 19, line 36, to column 23, line 56. However, the preferred zwitterionic cosurfactants herein are the ethoxylated zwitterionic compounds of the above patent and the biodegradable zwitterionic surfactants described in the pending U.S. patent application Ser. No. 114,184, Wentler, et al., filed Jan. 22, 1980, incorporated herein by reference.

A preferred weight ratio of the compounds herein to zwitterionic surfactant is from about 1:1 to about 4:1, preferably from about 2:1 to about 3:1.

The detergent compositions herein optionally, but preferably, also contain from about 1% to about 95%, preferably from about 5% to about 75%, by weight of detergent builder materials. Detergency builders are generally characterized by an ability to sequester or precipitate water hardness ions, particularly calcium and magnesium. They may also be used to maintain or assist in maintaining an alkaline pH in a washing solution.

All manner of detergency builders commonly taught for use in detergent compositions are suitable for use herein. Useful builders include any of the conventional inorganic and organic water-soluble builder salts. Such detergency builders can be, for example, water-soluble salts of phosphates, pyrophosphates, orthophosphates, polyphosphates, phosphonates, carbonates, polyhydroxysulfonates, silicates, polyacetates, carboxylates, polycarboxylates and succinates.

Specific examples of inorganic phosphate builders include sodium and potassium tripolyphosphates, phosphates, and hexametaphosphates. The polyphosphonates specifically include, for example, the sodium and potassium salts of ethylene diphosphonic acid, the sodium and potassium salts of ethane 1-hydroxy-1,1-diphosphonic acid and the sodium and potassium salts of ethane-1,1,2-triphosphonic acid. Examples of these and other phosphorus builder compounds are disclosed in U.S. Pat. Nos. 3,159,581; 3,213,030; 3,422,021; 3,422,137; 3,400,176 and 3,400,148, incorporated herein by reference.

Non-phosphorus containing sequestrants can also be selected for use herein as the detergency builder. Specific examples of non-phosphorus, inorganic builder ingredients include water-soluble inorganic carbonate, bicarbonate, and silicate salts. The alkali metal, e.g., sodium and potassium, carbonates, bicarbonates, and silicates are particularly useful herein.

Water-soluble, non-phosphorus organic builders are also useful herein. For example, the alkali metal, ammonium and substituted ammonium polyacetates, carboxylates, polycarboxylates and polyhydroxysulfonates are useful builders in the present compositions. Specific examples of the polyacetate and polycarboxylate builder salts include sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid.

Highly preferred polycarboxylate builders herein are set forth in U.S. Pat. No. 3,308,067, Diehl, incorporated herein by reference. Examples of such materials include the water-soluble salts of homoand copolymers of aliphatic carboxylic acids such as maleic acid, itaconic acid, mesaconic acid, fumaric acid, aconitic acid, citraconic acid and methylenemalonic acid.

Additional, preferred builders herein include the water-soluble salts, especially the sodium and potassium salts, of carboxymethyloxymalonate, carboxymethyloxysuccinate, cis-cyclohexanehexacarboxylate, cis-cyclopentanetetracarboxylate phloroglucinol trisulfonate, and the copolymer of maleic anhydride with vinyl methyl ether or ethylene.

Other suitable polycarboxylates for use herein are the polyacetal carboxylates fully described in U.S. Pat. No. 4,144,226, issued Mar. 13, 1979 to Crutchfield, et al., and U.S. Pat. No. 4,146,495, issued Mar. 27, 1979 to Crutchfield, et al., the disclosures of which are incorporated herein by reference. These polyacetal carboxylates can be prepared by bringing together under polymerization conditions an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

Another type of detergency builder material useful in the present compositions comprises a water-soluble material capable of forming a water-insoluble reaction product with water hardness cations in combination with a crystallization seed which is capable of providing growth sites for said reaction product. Such "seeded builder" compositions are fully disclosed in Belgian Pat. No. 798,856 issued Oct. 29, 1973, the disclosure of which is incorporated herein by reference. Specific examples of such seeded builder mixtures comprise: 3:1 wt. mixtures of sodium carbonate and calcium carbonate having 5 micron particle diameter; 2.7:1 wt. mixtures of sodium sequicarbonate and calcium carbonate having a particle diameter of 0.5 microns; 20:1 wt. mixtures of sodium sequicarbonate and calcium hydroxide having a particle diameter of 0.01 micron; and a 3:3:1 wt. mixture of sodium carbonate, sodium aluminate and calcium oxide having a particle diameter of 5 microns.

A further class of detergency builder materials useful in the present invention are the insoluble amorphous and crystalline aluminosilicates disclosed in the pending U.S. patent application of Rodriguez, et al., Ser. No. 049,704, filed June 18, 1979, incorporated herein by reference. Particularly useful aluminosilicates are those commonly known as Zeolites A, X, and P(B).

Highly preferred non-phosphorus builder materials herein include sodium carbonate, sodium bicarbonate, sodium silicate, sodium citrate, sodium oxydisuccinate, sodium mellitate, sodium nitrilotriacetate, sodium ethylenediaminetetraacetate, and the sodium aluminosilicates, and mixtures thereof.

The detergent compositions herein preferably have an in-use pH in an aqueous laundry liquor of from about 9.0 to about 11.0, more preferably from about 9.4 to about 10.4. This pH is preferably provided by alkali metal silicate builder materials. The alkali metal silicates also enhance particulate soil removal from laundered fabrics when included in the detergent compositions of this invention. Moreover, the silicates provide corrosion inhibition protection to the metal parts of washing machines. Finally, the silicates provide a certain degree of crispness and pourability to spray-dried detergent granules which is very desirable to avoid lumping and caking, particularly during prolonged storage.

The alkali metal silicates should represent from about 1% to about 15%, preferably from about 3% to about 8%, by weight of the detergent composition. The use of more than 10% by weight of the silicates in the spray-dried detergent compositions herein may present solubility problems in cold water usage conditions, especially when sodium aluminosilicate builders are also present in the detergent composition. U.S. Pat. No. 3,985,669, Krummel, et al., issued Oct. 12, 1976, incorporated herein by reference, discloses the preferred use of low levels of silicates in detergent compositions also containing aluminosilicate builders. However, admixing powdered alkali metal silicates with spray-dried granular compositions containing the aluminosilicates helps reduce interactions between the silicates and aluminosilicates and thus helps improve the solubility of granular detergents containing both components.

Suitable silicate solids have a molar ratio of $SiO_2$ to alkali metal oxide in the range from about 1:2 to about 4:1, preferably from about 1.6:1 to about 2.4:1. The alkali metal silicates suitable herein are commercial preparations of the combination of silicon dioxide and alkali metal oxide, fused together in varying proportions. Crystalline silicate solids normally possess a high alkalinity content; in addition hydration water is frequently present as, for example, in metasilicates which can exist having 5, 6 or 9 molecules of water. The alkalinity is provided through the monovalent alkali metal ions such as, for example, sodium, potassium, lithium and mixtures thereof. The sodium and potassium silicate solids are generally used. Thus, the preferred alkali metal silicates herein have a molar ratio of $SiO_2$:$M_2O$ of from about 1:2 to about 2.5:1 wherein M is sodium or potassium or mixtures thereof. Particularly preferred are the sodium silicates having an $SiO_2$:$Na_2O$ ratio of from about 1.6:1 to about 2.4:1.

An especially preferred builder system, suitable for providing the preferred in-use pH range, comprises from about 3% to about 8% by weight of the detergent composition of sodium silicate having a molar ratio of from about 1.6:1 to about 2.4:1 and from about 10% to about 30% by weight of the detergent composition of sodium carbonate. Such a builder system provides reserve alkalinity without undesirably reducing cold water solubility of the composition.

Granular detergent compositions herein preferably contain from about 20% to about 70% by weight of a detergent builder material selected from the group consisting of alkali metal phosphates, polyphosphates, carbonates, polyhydroxysulfonates, silicates, carboxylates, polycarboxylates, and aluminosilicates.

Liquid detergent compositions herein preferably contain the water-soluble detergency builders disclosed in the pending U.S. patent application of Leikhim, et al., Ser. No. 083,907, from page 6, line 21 to page 9, line 29. More particularly, the organic builders for use in liquid compositions are the polycarboxylates, polyacetates, aminopolycarboxylates and phosphonates. Inorganic builders suitable for use in the liquid compositions herein are the polyphosphates, and preferably the water-soluble pyrophosphates.

Other optional components for use in liquid compositions herein include those described in the above Leikhim, et al., application, particularly from page 11, line 14 to page 16, line 4.

Other ingredients which are conventionally used in detergent compositions can be included in the detergent compositions of the present invention. These components include color speckles, bleaching agents and bleach activators, suds boosters or suds suppressors, anti-tarnish and anti-corrosion agents, soil suspending agents, soil release agents, dyes, fillers, optical brighteners, germicides, pH adjusting agents, non-builder alkalinity sources, hydrotropes, enzymes, enzyme-stabilizing agents, perfumes, and other optional detergent compounds.

An especially preferred optional component in the present detergent compositions is the alkylene oxide condensation product described in pending U.S. patent application Ser. No. 117,904, Ferry, filed Feb. 4, 1980, particularly from page 9, line 28 through page 11, line 24, incorporated herein by reference. Such alkylene oxide condensation products, which preferably are the polyethylene glycols, are believed to enhance the cold water cleaning of the present detergent compositions, especially on hard to remove particulate/oily combination soils or stains, such as those found on pillowcases.

Since chlorine bleaches, such as the alkali metal hypochlorites, can oxidize the alpha-sulfoxide compounds herein, converting them to the corresponding alpha-sulfones, optional bleaching agents and alpha-sulfoxide compounds should be selected such that any alpha-sulfones formed in either the detergent compositions herein or in the laundering solution are not insoluble. For example, bleaching agents of the active oxygen-releasing type, such as any of the inorganic peroxygen bleaching compounds or the organic peroxy acids, do not oxidize sulfoxide groups and thus may be used with any of the alpha-sulfoxides herein. However, if chlorine bleaches are desired by the user, the alpha-sulfoxide compounds should be selected such that any alpha-sulfones formed are the soluble versions claimed herein, in which Y in the general formula is hydrogen, a water-soluble cation, or the $C_2$–$C_3$ alkylene oxide group. Of course, the alpha-sulfone compounds herein do not undergo further oxidation, and thus can be used with any bleaching agents.

The following non-limiting examples illustrate detergent compositions encompassed by the present invention.

All percentages, parts, and ratios used herein are by weight unless otherwise specified.

EXAMPLE I

The following are spray-dried granular detergent compositions according to the present invention.

| Component | A | B | C | D |
|---|---|---|---|---|
| Sodium $C_{13}$ linear alkylbenzene sulfonate | | 7.0 | 6.0 | |
| Sodium tallowalkyl sulfate | 5.5 | | | |
| Sodium $C_{14-15}$ alkyl ethoxylate (2.25) sulfate | 5.5 | | | |
| Sodium alpha-methylsulfinyl tallowate | 7.0 | | 12.0 | |
| Sodium alpha-methylsulfinyl cocoate | | 10.0 | | 15.0 |
| Sodium tripolyphosphate | 24.4 | 33.0 | | 18.0 |
| Sodium aluminosilicate (hydrated Zeolite A, particle diameter 1-10 microns) | 18.0 | | 18.0 | |
| Sodium nitrilotriacetate | | | 25.0 | 18.0 |
| Sodium carbonate | 10.1 | | 18.0 | |
| Sodium silicate (2.Or) | 2.0 | 6.0 | 2.0 | 6.0 |
| Sodium sulfate | 16.8 | 32.0 | 16.0 | 30.0 |
| Polyethylene glycol 6000 | 0.9 | 0.9 | 0.9 | 2.0 |
| Water and miscellaneous | Balance to 100 | | | |

The above compositions are produced by admixing all components, exept the polyethylene glycol, in a crutcher to form a homogeneous mix, which is then spray-dried in a conventional manner. The polyethylene glycol is then admixed with the spray-dried granules to form the final detergent compositions.

Compositions A-D are added, at a level of about 1400 parts per million (ppm), to standard top-loading automatic washing machines containing water having a temperature of about 16° C. and a hardness of about 7 grains/gallon (2 moles $Ca^{++}$:1 mole $Mg^{++}$). Loads of mixed fabrics are laundered in the resulting solutions, which have a pH of about 9.7, using the machine manufacturer's instructions. The fabrics are then rinsed and dried.

Compositions A-D provide superior cleaning of greasy/oily type soils in the 16° C. wash water. Compositions A-C, containing anionic cosurfactants, also provide outstanding cleaning on particulate and clay soils.

EXAMPLE II

The following are spray-dried granular detergent compositions according to the present invention.

| Component | A | B | C | D |
|---|---|---|---|---|
| Zwitterionic surfactant[1] | 6.0 | | | |
| Zwitterionic surfactant[2] | | 6.0 | | 9.0 |
| 3-(N-coconutalkyl N,N-dimethyl ammonio)-2-hydroxy propane-1-sulfonate | | | 5.0 | |
| Sodium alpha-methylsulfinyl tallowate | | 12.0 | | 9.0 |
| Sodium alpha-methylsulfinyl cocoate | 12.0 | | 15.0 | |
| Sodium tripolyphosphate | 32.0 | | 18.0 | 25.0 |
| Sodium aluminosilicate (hydrate Zeolite A, particle diameter 1-10 microns) | | 12.0 | 18.0 | |
| Sodium nitrilotriacetate | | 32.0 | | 12.0 |
| Sodium carbonate | | 10.0 | 18.0 | 14.0 |
| Sodium silicate (2.0r) | 6.0 | 2.0 | 3.0 | 6.0 |
| Sodium sulfate | 32.0 | 14.0 | 10.0 | 14.0 |
| Polyethylene glycol 6000 | 0.9 | | 2.0 | |
| Water and miscellaneous | Balance to 100 | | | |

[1] $C_{18}H_{35}(CH_3)_2{}^+N—(CH_2CH_2O)_9CH_2CH_2SO_3{}^-$

[2] 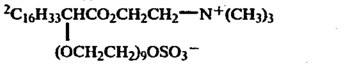

The above compositions are prepared and used in the manner of Example I. The compositions also provide outstanding cleaning, both of particulate and oily soils, under cold water laundering conditions.

Substantially similar cleaning performance is obtained when the sodium alpha-methylsulfinyl tallowate and cocoate compounds in Examples I and II are each replaced with the corresponding laurate, myristate, palmitate, stearate and eicosanoate compounds. Comparable results are also obtained when the sodium in any of the above alpha-sulfoxide compounds is replaced with hydrogen, potassium, ethyl, methyl, propyl and ethylene oxide groups containing 1, 2, 3, 5, 7 and 10 ethylene oxide units.

Comparable cleaning is also provided when the sodium alpha-methylsulfinyl tallowate and cocoate compounds in Examples I and II are each replaced with alpha-sulfoxide compounds of the formula

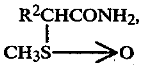

where $R^2$ is a $C_6$, $C_8$, $C_{10}$, $C_{12}$, $C_{14}$, $C_{16}$ and $C_{18}$ alkyl group. Similar performance is provided when one or both of the hydrogen atoms of the amide group in any of the above compounds is replaced with methyl, ethyl, propyl and ethylene oxide groups containing 1, 2, 3, 5, and 8 ethylene oxide units.

Substantially similar cleaning performance is obtained when the sodium alpha-methylsulfinyl tallowate and cocoate compounds in Examples I and II are each replaced with alpha-sulfone compounds of the formula

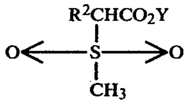

where $R^2$ is a $C_6$, $C_8$, $C_{10}$, $C_{12}$, $C_{14}$, $C_{16}$, and $C_{18}$ alkyl group, and Y is hydrogen, sodium, and an ethylene oxide group containing 1, 3, 5, 7 and 10 ethylene oxide units.

EXAMPLE III

The following are liquid detergent compositions according to the present invention.

| Component | A | B | C |
|---|---|---|---|
| Magnesium $C_{12}$ linear alkyl benzene sulfonate | 20.0 | | |
| Zwitterionic surfactant [1] (from Example II) | | 12.0 | 15.0 |
| Methyl alpha-methylsulfinyl cocoate | 20.0 | 25.0 | |
| Methyl alpha-methylsulfinyl palmitate | | | 15.0 |
| Sodium citrate | | | 10.0 |
| Potassium toluene sulfonate | | | 12.0 |
| Triethanol amine | 3.0 | 3.0 | 3.0 |
| Coconut fatty acid | 1.0 | | |
| Ethanol | 6.5 | 12.0 | 4.0 |
| Water and miscellaneous | Balance to 100 | | |

The above compositions are prepared simply by mixing the components. They also provide outstanding particulate and oily soil removal performance under cold water usage conditions.

Substantially similar cleaning performance is obtained when the methyl alpha-methylsulfinyl palmitate and cocoate compounds in the above compositions are each replaced with the corresponding laurate, myristate, tallowate, stearate and eicosanoate compounds. Comparable results are also obtained when the methyl group attached to the ester linkage in any of the above alpha-sulfoxide compounds is replaced with hydrogen, sodium, potassium, ethyl, propyl, and ethylene oxide groups containing 1, 2, 4, 6, and 9 ethylene oxide units.

Comparable cleaning is also provided when the methyl alpha-methylsulfinyl palmitate and cocoate compounds in the above compositions are each replaced with alpha-sulfoxide compounds of the formula

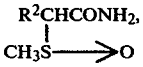

where $R^2$ is a $C_6$, $C_8$, $C_{10}$, $C_{12}$, $C_{14}$, $C_{16}$ and $C_{18}$ alkyl group. Similar performance is provided when one or both of the hydrogen atoms of the amide group in any of the above compounds is replaced with methyl, ethyl, propyl and ethylene oxide groups containing 1, 2, 3, 5, 6, 8 and 10 ethylene oxide units.

Substantially similar cleaning performance is obtained when the methyl alpha-methylsulfinyl palmitate and cocoate compounds in the above compositions are each replaced with alpha-sulfone compounds of the formula

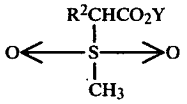

where $R^2$ is a $C_6$, $C_8$, $C_{10}$, $C_{12}$, $C_{14}$, $C_{16}$, and $C_{18}$ alkyl group, and Y is hydrogen, sodium, and an ethylene oxide group containing 1, 3, 5, 7 and 10 ethylene oxide units.

What is claimed is:

1. A compound of the formula:

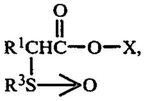, 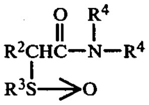 or 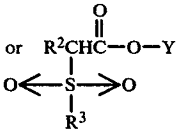

wherein $R^1$ is a $C_{10}$–$C_{18}$ hydrocarbyl group; $R^2$ is a $C_6$–$C_{18}$ hydrocarbyl group; $R^3$ is a $C_1$–$C_4$ hydrocarbyl group; each $R^4$ is hydrogen, a $C_1$–$C_4$ hydrocarbyl group, or a $C_2$–$C_3$ alkylene oxide group, or mixtures thereof, containing from about 1 to about 10 alkylene oxide units; X is an $R^4$ group or a water-soluble metal, ammonium or substituted ammonium cation; and Y is hydrogen, a water-soluble metal, ammonium or substituted ammonium cation or a $C_2$–$C_3$ alkylene oxide group, or mixtures thereof, containing from about 1 to about 10 alkylene oxide units.

2. A compound according to claim 1 wherein $R^1$ is a $C_{10}$–$C_{14}$ alkyl group and $R^2$ is a $C_8$–$C_{14}$ alkyl group.

3. A compound according to claim 2 wherein $R^1$ is a $C_{10}$–$C_{12}$ alkyl group and $R^2$ is a $C_8$–$C_{12}$ alkyl group.

4. A compound according to claims 1 or 2 wherein the $C_2$–$C_3$ alkylene oxide group is an ethylene oxide group containing from about 1 to about 5 ethylene oxide units.

5. A compound according to claims 1 or 2 wherein X and Y are each hydrogen or a water-soluble alkali metal cation.

6. A compound according to claim 5 wherein X and Y are sodium.

7. A compound according to claims 1 or 2 wherein each $R^4$ is hydrogen or a methyl or ethyl group.

8. A compound according to claims 1 or 2 wherein $R^3$ is a methyl or ethyl group.

9. A compound of the formula:

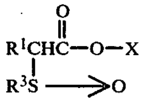

wherein $R^1$ is a $C_{10}$–$C_{18}$ hydrocarbyl group, $R^3$ is a $C_1$–$C_4$ hydrocarbyl group, and X is hydrogen or a water-soluble alkali metal cation.

10. A compound according to claim 9 wherein $R^1$ is a $C_{10}$–$C_{14}$ alkyl group.

11. A compound according to claim 10 wherein $R^1$ is a $C_{10}$–$C_{12}$ alkyl group.

12. A compound according to claims 9 or 10 wherein $R^3$ is a methyl or ethyl group.

13. A compound according to claim 12 wherein X is sodium.

14. A compound of the formula:

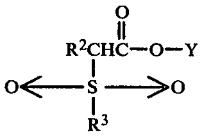

wherein $R^2$ is a $C_6$–$C_{18}$ hydrocarbyl group, $R^3$ is a $C_1$–$C_4$ hydrocarbyl group, and Y is hydrogen, a water-soluble alkali metal cation, or an ethylene oxide group containing from about 1 to about 5 ethylene oxide units.

15. A compound according to claim 14 wherein $R^2$ is a $C_8$–$C_{14}$ alkyl group.

16. A compound according to claim 15 wherein $R^2$ is a $C_8$–$C_{12}$ alkyl group.

17. A compound according to claims 14 or 15 wherein $R^3$ is a methyl or ethyl group.

18. A compound according to claim 17 wherein Y is sodium.

* * * * *